(12) United States Patent
Legay et al.

(10) Patent No.: US 6,253,106 B1
(45) Date of Patent: Jun. 26, 2001

(54) CONFIGURABLE MULTISITE ACTIVE IMPLANTABLE MEDICAL DEVICE

(75) Inventors: Thierry Legay, Fontenay les Briis; Anne Bouhour, Ville d'Avray; Alain Ripart, Gif sur Yvette, all of (FR)

(73) Assignee: Ela Medical S.A., Montrouge (FR)

( * ) Notice: Subject to any disclaimer, the term of this patent is extended or adjusted under 35 U.S.C. 154(b) by 0 days.

(21) Appl. No.: 09/218,678

(22) Filed: Dec. 22, 1998

(30) Foreign Application Priority Data

Dec. 23, 1997 (FR) .................................................. 97 16378

(51) Int. Cl.$^7$ ............................. A61N 1/362; A61N 1/368
(52) U.S. Cl. ...................................... 607/9; 607/5
(58) Field of Search ................... 607/5, 9, 122, 607/15

(56) References Cited

U.S. PATENT DOCUMENTS

| | | | |
|---|---|---|---|
| 5,107,834 | * 4/1992 | Ideker et al. ............................... | 607/5 |
| 5,360,435 | 11/1994 | DeGroot ................................... | 607/7 |
| 5,376,105 | * 12/1994 | Hedberg ................................... | 607/5 |
| 5,792,203 | 8/1998 | Schroppel ............................... | 607/30 |
| 5,800,465 | * 9/1998 | Thompson et al. ....................... | 607/9 |
| 6,070,100 | * 5/2000 | Bakels et al. . | |

FOREIGN PATENT DOCUMENTS

| | | | |
|---|---|---|---|
| 0030897 | 8/1987 | (EP) | ............................. A61N/1/362 |
| 0308536 | 3/1989 | (EP) | ............................. A61N/1/368 |
| 0598617 | 5/1994 | (EP) | ............................. A61N/1/39 |
| 2079610 | 1/1982 | (GB) | ............................. A61N/1/36 |

* cited by examiner

Primary Examiner—Carl H. Layno
(74) Attorney, Agent, or Firm—Orrick, Herrington & Sutcliffe LLP

(57) ABSTRACT

An active implantable medical device, especially a cardiac pacemaker, defibrillator and/or cardiovertor, of the configurable multisite type. In this multisite device, electrodes are placed in at least three distinct myocardial sites for stimulation (12, 14, 20, 22), of which at least one is a site for ventricular stimulation/detection (14, 22), these electrodes being connected to independent outputs (DA, DV, Da1, Dv2) of the multisite device in a manner as to allow the application of stimulation pulses produced by a plurality of distinct stimulation stages (24, 26, 28, 30). The number of stimulation output stages is at most equal to the number of stimulation sites. The device also includes switches (SA, SV, S1, S2) to connect selectively and according to one of various possible stimulation configurations, the stimulation stages, or selected ones of the stimulation stages, to the various sites of stimulation, or to selected ones of the stimulation sites. The switches can be controlled to modify the stimulation configuration as between the various possibilities in a manner as to research (to identify) the one considered as optimal among the possible variations, which can then be selected.

6 Claims, 1 Drawing Sheet

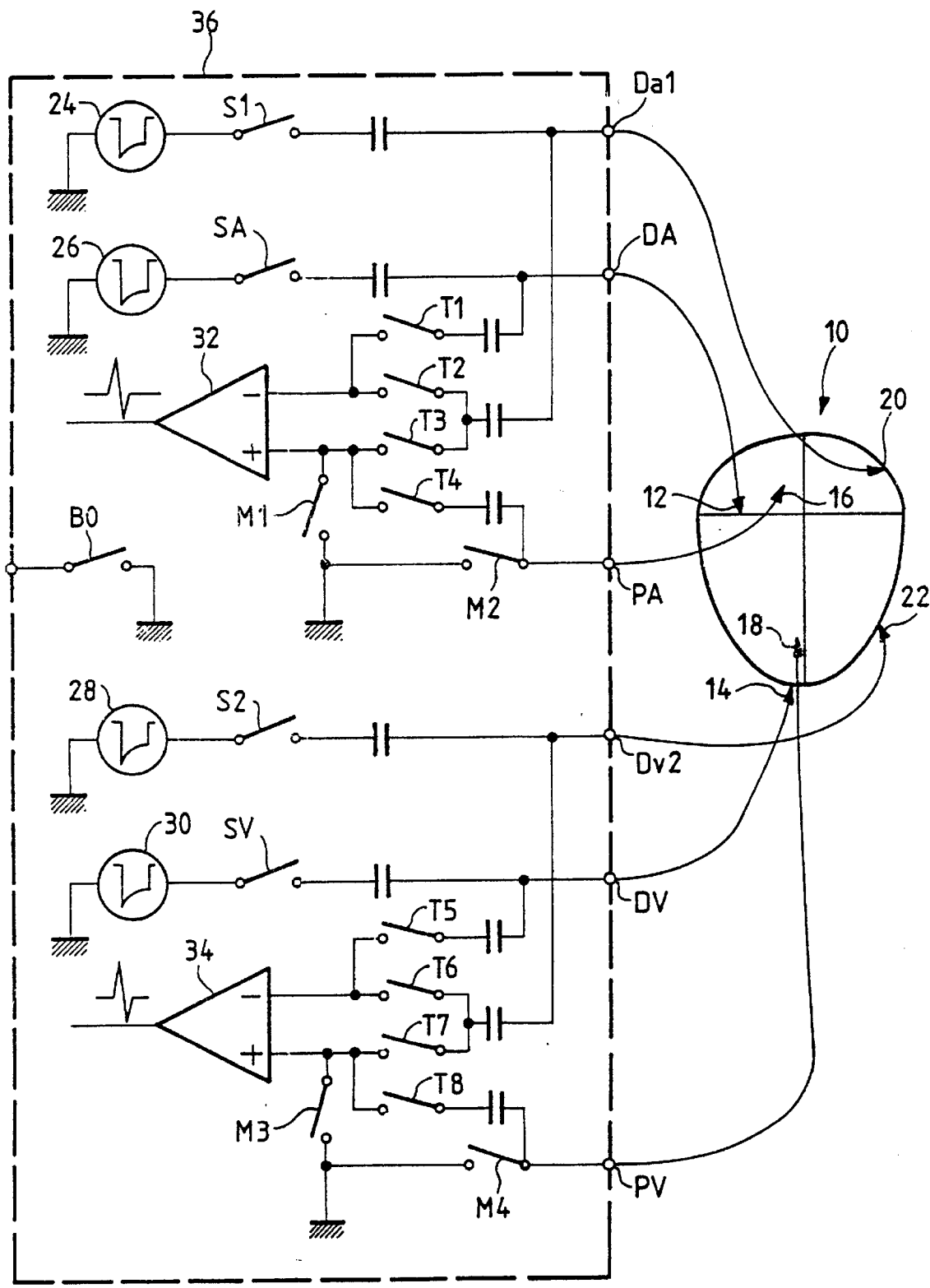

US 6,253,106 B1

CONFIGURABLE MULTISITE ACTIVE IMPLANTABLE MEDICAL DEVICE

FIELD OF THE INVENTION

The present invention concerns "active implantable medical devices" such as those defined by the Jun. 20, 1990 directive 90/385/EEC of the European Community Council, particularly devices such as cardiac pacemakers, defibrillators and/or cardiovertors capable of delivering a low energy electrical stimulus to the heart for the treatment of the so-called "troubles of the cardiac rhythm," namely cardiac arrhythmias.

The invention concerns more particularly the so-called "multisite" prostheses, that is prostheses in which electrodes are placed in a plurality of distinct respective sites, of which at least two are ventricular sites. These prostheses can be of the "single chamber" (double ventricular stimulation), triple chamber (right atrial stimulation and double ventricular stimulation) or even quadruple chamber (double atrial stimulation and double ventricular stimulation) type. The electrodes are connected to independent outputs of the pacemaker in a manner that permits the detection of depolarization potentials, as well as the application of stimulation pulses.

BACKGROUND OF THE INVENTION

Multisite cardiac pacemakers are known. EP-A-0 030 897 describes such multisite pacemakers, in which there are two outputs and the corresponding stimulation electrodes are implanted in two predetermined sites belonging to the same cardiac cavity, notably the ventricle. A switching device allows one to choose the functioning mode of the pacemaker among various modes (bipolar, double unipolar, double unipolar or bifocal ventricular), nevertheless without modifying the implantation of electrodes and the choice of stimulation sites.

OBJECTS AND SUMMARY OF THE INVENTION

It is an object of the present invention to propose a cardiac pacemaker (or a stimulation circuit for a defibrillator or cardiovertor) of the multisite type allowing, without any notable increase of the complexity of the pacemaker circuit, to modify the choice from among the installed sites by researching, (i.e., evaluating and/or determining) an optimal stimulation configuration. Indeed, when one modifies the configuration of stimulation sites after a certain time, one detects (observes) a best recovery of the muscular tonus of the myocardium, and therefore a reduction of the effort required to be provided by the muscle.

For the treatment of dilated cardiomyopathy, the goal is to have several poles of stimulation. The ability to be able to modify the configuration is a distinct practical advantage provided by the present invention.

The multiplication of the number of sites normally would entail a correlative multiplication of the number of stimulation circuits and detection circuits, that would reach rapidly the constraints imposed by the available space inside (volume) the case of the pacemaker, given the increase of the number of components. In addition and especially, the increase of the number of components would induce a significant increase of the current consumption of the pacemaker, susceptible to reduce the nominal life duration of the pacemaker to below the required limit (or require more powerful and likely larger batteries).

The present invention aims to solve these aforementioned difficulties, by proposing a configurable multisite, active implantable medical device, preferably a pacemaker, endowed with a stimulation/detection capacity that is susceptible to stimulate and to detect according to multiple configurations, and modifiable at will, while minimizing the quantity of necessary components. Thus, the invention seeks to realize a compromise between, on the one hand, clinical requirements and, on the other hand, constraints of volume inside the implant case and constraints of circuit construction and energy consumption.

To this end, the present invention is directed to an active implantable medical device, in which electrodes are placed in at least three distinct myocardial sites for stimulation, of which at least one site is a ventricular stimulation and ventricular detection site. These electrodes are connected to independent outputs of the device in a manner to allow the application of stimulation pulses produced by a plurality of distinct stimulation stages (i.e., low energy pulse generating circuits), which circuits are in number at most equal to the number of stimulation sites. The invention is characterized in that it also comprises a commutation means, i.e., a network of switches, to connect selectively and according to one of a number of various possible stimulation configurations, the stimulation stages, or selected ones of the stimulation stages, to the various stimulation sites, or to selected ones of the stimulation sites, and a means of controlling the commutation means, to modify the stimulation configuration in a manner as to research the configuration considered to be optimal.

This device also can comprise at least two distinct detection stages (cardiac event detection circuits) for the detection of spontaneous electrical activity in a cardiac cavity, in which the commutation means comprises, in addition, means for connecting selectively and according to one of a number of various possible detection configurations the detection stages, or selected ones of the detection stages, to the various stimulation sites or to selected ones of the stimulation sites which connection(s) to a detection stage may or may not be concurrent with a connection to a stimulation stage. In other words, a detection stage may be connected to the same site as a stimulation stage, but not every site connected to a stimulation stage is also connected to a detection stage.

Advantageously, the means of control of the commutation means can operate dynamically during functioning of the device, in a manner as to modify the configurations for the stimulation and/or detection, and the device comprises in addition means for evaluation of the result obtained by each selected configuration to perform the aforementioned research of an optimal configuration.

BRIEF DESCRIPTION OF THE DRAWING

Other characteristics, features and advantages of the invention will appear to the person of ordinary skill in the art in view of the following detailed description of a preferred embodiment, made with reference to the annexed drawing FIGURE, which is a schematic diagram of a pacemaker realized according to teaching of the present invention, and a plurality of leads implanted in various sites of a myocardium.

DETAILED DESCRIPTION OF THE DRAWING

With reference to the drawing, the reference 10 designates, schematically and in a general manner, the myocardium, on which are implanted various leads in a plurality of sites 12, 14, 16, 18, 20 and 22. It is preferred that the electrodes are in effective contact with the myocardium, such that each of electrodes 12, 14, 20 and 22 is in contact with each of the four cavities of the myocardium. It also is preferred to have, in addition, floating electrodes, such as electrodes 16 and 18, which can be used to serve as reference potentials to detect signals or to stimulate, when the stimulation is operated in a bipolar mode. These floating electrodes can be, for example, constituted by the proximal electrode of a bipolar lead, the distal extremity of which is in contact with the cavity.

Thus, in the configuration of electrodes illustrated on the figure, electrodes 12 and 16 are those of a bipolar lead implanted in the right atrium, electrodes 14 and 18 are the ones of a bipolar lead implanted in the right ventricle, the electrode 20 is the one of a unipolar lead implanted in the left atrium, and the electrode 22 is the one of a unipolar lead implanted in the left ventricle.

This configuration is, however, in no manner meant to be restrictive concerning the number of electrodes, as well as the manner of their configuration, as long as one has at least three stimulation/detection sites, of which at least one is in the ventricle. Furthermore, the leads (electrodes in contact with the myocardium or floating electrodes), need not necessarily be placed in cardiac cavities, but also can be situated in sites which allow one to stimulate cavities in an indirect manner. For example, leads implanted in a coronary sinus, or alternately at the exterior of the myocardium (e.g., an epicardial lead) can be used.

One of the advantageous characteristics of the invention is indeed to have a system where electrodes are no longer dedicated to particular cardiac cavities, but rather, can be placed such that it does not matter in which cardiac cavity the lead is placed. Indeed, it is possible even to place all electrodes in the same cavity, for example, in the right ventricle, with one electrode located in the septum such that it would be able to stimulate the left ventricle, and/or with an electrode the separation wall of cavities, etc.

Concerning the pacemaker, in the illustrated example, it comprises (here again, in a nonrestrictive manner) four independent poles, allowing each pole to deliver an electrical stimulation, which is programmable in amplitude and in width, to four points of the heart, and two poles, typically of proximal electrodes, serving as reference potentials for the stimulation and the detection. By convention, the six poles of the device are designated according to a typical utilization as illustrated, although this constitutes in no case a limit to the various possibilities of the system, since each of the poles can be connected to a site situated in any cardiac cavity.

One will designate the poles as follows:
  DA and DV (Distal Atrial and Distal Ventricular), the poles connected to electrodes 12 and 14,
  PA and PV (Proximal Atrial and Proximal Ventricular), the poles connected to electrodes 16 and 18,
  Da1 (Distal atrial), the pole connected to the electrode 20, that is the first additional pole (No. 1) as compared to a double chamber device, and
  Dv2 (Distal ventricular) the pole connected to the electrode 22, that is the second additional pole (No. 2) as compared to a double chamber device.

The pacemaker comprises four stimulation stages 24, 26, 28 and 30 and two detection circuits, with respective amplifiers 32 and 34.

Various electronic switches SA, SV, S1, S2, M1–M4 and T1–T8 are connected in the manner represented on the figure between stages of stimulation 24, 26, 28 and 30, and stages of detection 32 and 34, on the one hand, and the six poles DA, PA, Da1, DV, PV, Dv2, on the other hand. They allow a further connection of the these six poles to each of stages 24 to 34, so as to realize various stimulation configurations and various configurations for the detection of the cardiac signal.

It also is foreseen to have a switch B0 allowing one to connect the metallic case 36 of the device to the ground of the system electronics, when one wishes to realize a stimulation or a detection between a endocardiac pole and the ground of the case.

Set forth below are various stimulation and detection configurations that can be realized by means of these different switches. The various modes of detection and stimulation will be designated as follows:
  "unipolar detection" ("Det. unip.") is a detection between an endocardiac pole and the case,
  "bipolar detection" ("Det. bip.") is a differential detection between two endocardiac poles (the case constituting a reference for the common mode),
  "tripolar detection" ("Det. trip.") is a detection on two endocardiac poles connected between them, referenced to a third endocardiac pole (the case constituting a reference for the common mode),
  "unipolar stimulation" ("Stim. unip.") is a stimulation between an endocardiac pole and the case,
  "bipolar stimulation" ("Stim. bip.) is a stimulation between two endocardiac poles of which one is at ground (case not connected).

In the case of a classic DDD pacemaker (double chamber), the term "bipolar" ("bip.") refers to two endocardiac poles situated in the same cavity, but in the case of a multisite pacemaker (MS), this is no longer the case. One will call by convention "quasi-bipolar" ("quasi-bip.") a configuration with two endocardiac electrodes in two different cavities, and similarly for "quasi-tripolar" ("quasi-trip."). The different possibilities of configuration are given by the following Table, that indicates: (1) the configuration considered, (2) poles (electrodes) implied, (3) the fact that it concerns an already known configuration such as in a classic double chamber (DDD) pacemaker, or a new configuration, specific to the multisite (MS) device of the present invention, (4) switches to be closed, and (5) switches to be opened.

| Table | Configuration | Type | Closed | Open |
| --- | --- | --- | --- | --- |
| Det. unip. | Da1 | MS | B0, M1, T2 | M2, T1, T3, T4 |
| Det. quasi-bip. | Da1/PA | MS | B0, T2, T4 | M1, M2, T1, T3 |
| Det. quasi-bip. | DA/Da1 | MS | B0, T1, T3 | M1, M2, T2, T4 |
| Det. quasi-trip. | [DA + Da1]/PA | MS | B0, T1, T2, T4 | M1, M2, T3 |
| Det. bip. | DA/PA | DDD | B0, T1, T4 | M1, M2, T2, T3 |
| Det. unip. | DA | DDD | B0, M1, T1 | M2, T2, T3, T4 |
| Stim. unip. | Da1 | MS | B0, S1 | M2, M4 |
| Stim. quasi-bip. | Da1/PA | MS | M2, S1 | B0, M4 |
| Stim. unip. | DA | DDD | B0, SA | M2, M4 |
| Stim. bip. | DA/PA | DDD | M2, SA | B0, M4 |
| Det. unip. | Dv2 | MS | B0, M3, T6 | M4, T5, T7, T8 |
| Det. quasi-bip. | Dv2/Pv | MS | B0, T6, T8 | M3, M4, T5, T7 |
| Det. quasi-bip. | DV/Dv2 | MS | B0, T5, T7 | M3, M4, T6, T8 |

-continued

| Table | Configuration | Type | Closed | Open |
|---|---|---|---|---|
| Det. quasi-trip. | [DV + Dv2]/PV | MS | B0, T5, T6, T8 | M3, M4, T7 |
| Det. bip. | DV/PV | DDD | B0, T5, T8 | M3, M4, T6, T7 |
| Det. unip. | DV | DDD | B0, M3, T5 | M4, T6, T7, T8 |
| Stim. unip. | Dv2 | MS | B0, S2 | M2, M4 |
| Stim. quasi-bip. | Dv2/PV | MS | M4, S2 | B0, M2 |
| Stim. unip. | DV | DDD | B0, SV | M2, M4 |
| Stim. bip. | DV/PV | DDD | M4, SV, | B0, M2 |

One will appreciate from the foregoing table that there are shown - but in a non exhaustive manner, for the stimulation, eight different configurations of which four are new, and, for the detection, twelve possible configurations of which eight are new.

In practice, the selection of the location of the electrodes in the various parts of the four cardiac cavities is left to the choice of the medical practitioner.

The configurations of stimulation and detection are thus realized, either according to the indications (selections) of the medical practitioner, or in an automatic manner, by research of the preferential configuration. Thus, switches can be programmed (e.g., using a suitable software program) in a manner as to modify dynamically the configuration during the functioning of the pacemaker, so as to adapt dynamically the pacemaker in order to be in the best configuration. In this regard, the configuration is considered as "best" if it obtains an improvement of a cardiac parameter, such as the flow rate (relating to the performance obtained by the other possible configuration). The automatic research can be initiated on a periodic basis, on a prompt from a medical practitioner using a remote programmer. Reference in this regard is made to EP 0862927 and its corresponding U.S. Pat. No. 5,995,870, issued from application Ser. No. 09/036,330, which were copending and are commonly assigned with the invention hereof.

Stimulation on each of the four chosen poles are controlled by a certain number of parameters, notably delays, as follows:

delay between stages, namely between the atrial stage A and the ventricular stage V, by the atrio-ventricular delay which is well known in a DDD pacemaker, delay between cavities of the same stage, namely between DA and Da1 or between DV and Dv2, delay DA-Da1 and DV-Dv2 also being able, following the suitable programming of the pacemaker, to be reversed, namely delays Da1-DA or Dv2-DV, subsequent to the location of leads in the heart, that the medical practitioner will have to specify at the implantation of the device, a certain number of new preferential modes of stimulation which are proposed, accompanied by programmable parameters of temporal coupling.

Delays between stages, and similarly delays between cavities, can be, for example, programmable values of from 0 to 300 ms, preferably by steps of 8 ms (related to the microprocessor clock cycle). For each pole that is able to deliver an electrical stimulation, the parameters of the stimulus amplitude are accessible in an independent manner as are well known. It should be understood that the various switches are programmable under software control, using known electronic circuit structures and techniques as are known to persons of ordinary skill in the art. It also should be understood that the invention is preferably implemented using a hardware architecture that includes a microprocessor executing programming instructions to control the stimulation and detection in a manner well known, subject to the modifications thereto introduced by the present invention, which modifications are self-apparent to a person of ordinary skill in the art.

The research for the optimal or best configuration can be manual or automatic, such that the device can be sequenced through the range of possible configurations until the optimal or best is determined, and then selected by appropriate setting of the plurality of switches. The parameter to be optimized can be measured by the implanted device or in conjunction with a remote programmer or remote monitoring equipment coupled to the patient.

One further advantage of the present invention is to provide a multisite configuration that decreases the number of electrical outputs on the pacemaker case relative to prior art multisite devices. In a true four-chamber device having a bipolar configuration for each lead, eight outputs are necessary. The present invention, however, reduces the number of outputs needed to six. As a result, the number of connection feed-throughs in the connector head portion, and the size of the connector head portion of the pacemaker, are reduced. Similarly, in the case of a double ventricular MSO pacing system with one atrial stage, only five outputs are needed (DA, PA, atrial; PV, DV, VD2 ventricular).

One skilled in the art will appreciate that the present invention can be practiced by other than the prescribed embodiments, which are presented for purposes of illustration and not of limitation.

We claim:

1. An active implantable medical device, of a cardiac pacemaker, defibrillator and/or cardiovertor type, in which electrodes are to be placed in at least three myocardial stimulation sites (12, 14, 20, 22), of which at least one site is a ventricular stimulation and ventricular detection site (14, 22), the electrodes being connected to corresponding independent outputs (DA, DV, Da1, Dv2) of the device, in a manner as to allow the application of low-energy stimulation pulses produced by a plurality of distinct stimulation stages (24, 26, 28, 30), the plurality of stimulation stages comprising a number of stages that is at most equal to said at least three stimulation sites, said device characterized in that it comprises commutation means (SA, SV, S1, S2) to connect selectively and according to a plurality of possible configurations the stimulation stages for stimulation, or a selected one of the stimulation stages, to the various stimulation sites, or to a selected one of the stimulation sites, and means for controlling the commutation means to modify the stimulation configuration in a manner as to research an optimal configuration.

2. The device of claim 1 in which the control means of the commutation means operates dynamically during functioning of the device to modify the configurations of stimulation and/or detection, the device comprising in addition means for evaluating the research of the forementioned optimal configuration.

3. The device of claim 1, further comprising at least two distinct stages (32, 34) for the detection of spontaneous electrical activity in a cardiac cavity, and in which commutation means comprise in addition means (M1–M4, T1–T8) for connecting selectively and according to various possible detection configurations, at least one of the detection stages to at least one of the stimulation sites exclusively or concurrently with a connection to a stage of stimulation.

4. The device of the claim 3, in which the control means of the commutation means operates dynamically during functioning of the device to modify the configurations of stimulation and/or detection, the device comprising in addition means for evaluating the research of the aforementioned optimal configuration.

5. An active implantable medical device, of a cardiac pacemaker, defibrillator and/or cardiovertor type, in which electrodes are to be placed in at least three myocardial stimulation sites, of which at least one site is a ventricular stimulation and ventricular detection site, the electrodes being connected to corresponding independent outputs of the device, in a manner as to allow the application of stimulation pulses produced by a plurality of distinct stimulation stages, the plurality of stimulation stages comprising a number of stages that is at most equal to said at least three stimulation sites, said device characterized in that it comprises commutation means to connect selectively and according to a plurality of possible configurations the stimulation stages for stimulation, or a selected one of the stimulation stages, to the various stimulation sites, or to a selected one of the stimulation sites, and means for controlling the commutation means to modify the stimulation configuration in a manner as to research an optimal configuration; wherein the control means of the commutation means operates dynamically during functioning of the device to modify the configurations of stimulation and/or detection, the device comprising in addition means for evaluating the research of the aforementioned optimal configuration.

6. The device of claim 5, further comprising at least two distinct stages for the detection of spontaneous electrical activity in a cardiac cavity, and in which commutation means further comprise means for connecting selectively and according to various possible detection configurations, at least one of the detection stages to at least one of the stimulation sites exclusively or concurrently with a connection to a stage of stimulation.

* * * * *

UNITED STATES PATENT AND TRADEMARK OFFICE
CERTIFICATE OF CORRECTION

PATENT NO. : 6,253,106 B1
DATED : June 26, 2001
INVENTOR(S) : Jean-Luc Bonnet and Marcel Limousin It is certified that error appears in the above-identified patent and that said Letters Patent is hereby corrected as shown below:

Column 4,
Line 4, delete "of the these" and insert -- of these -- therefor;

Column 5,
Line 40, delete "poles are" and insert -- poles is -- therefor; and

Column 6,
Line 66, delete "of the claim" and insert -- of claim -- therefor.

Signed and Sealed this

Twenty-sixth Day of July, 2005

JON W. DUDAS
*Director of the United States Patent and Trademark Office*